(12) United States Patent
Yamamoto et al.

(10) Patent No.: US 10,422,295 B2
(45) Date of Patent: Sep. 24, 2019

(54) APPARATUS FOR DETERMINING WHETHER THERE IS MALFUNCTION IN FILTER DEVICE

(71) Applicant: DENSO CORPORATION, Kariya, Aichi-pref. (JP)

(72) Inventors: Masahiro Yamamoto, Kariya (JP); Manabu Yoshidome, Kariya (JP); Masayuki Tamura, Kariya (JP); Go Miyagawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/740,919

(22) PCT Filed: Jun. 30, 2016

(86) PCT No.: PCT/JP2016/069526
§ 371 (c)(1),
(2) Date: Dec. 29, 2017

(87) PCT Pub. No.: WO2017/002942
PCT Pub. Date: Jan. 5, 2017

(65) Prior Publication Data
US 2018/0187623 A1   Jul. 5, 2018

(30) Foreign Application Priority Data
Jul. 1, 2015 (JP) .................. 2015-132866

(51) Int. Cl.
*F02D 41/22* (2006.01)
*F01N 3/02* (2006.01)
(Continued)

(52) U.S. Cl.
CPC .......... *F02D 41/222* (2013.01); *F01N 3/021* (2013.01); *F01N 3/023* (2013.01); *F01N 9/002* (2013.01);
(Continued)

(58) Field of Classification Search
CPC .......... F01N 11/00; F01N 13/008; F01N 3/01; F01N 3/023; F01N 9/002;
(Continued)

(56) References Cited

U.S. PATENT DOCUMENTS 9,863,301 B2 * 1/2018 Yoshidome ............. F01N 11/00
2008/0282682 A1 * 11/2008 C ....................... B01D 46/0086
60/277

(Continued)

*Primary Examiner* — Patrick D Maines
*Assistant Examiner* — Dapinder Singh
(74) *Attorney, Agent, or Firm* — Nixon & Vanderhye P.C.

(57) ABSTRACT

A filter malfunction determination apparatus includes a calculator that calculates, upon determination that a rapid output increase has occurred, an amount of change of a parameter value output from a sensor before and after the rapid output increase. The calculator calculates, based on the calculated amount of change, a correction value for correcting at least one of the parameter value output from the sensor and a malfunction determination threshold. The filter malfunction determination apparatus includes an offset corrector configured to perform, based on the correction value, offset correction of at least one of the parameter value output from the sensor and the malfunction determination threshold after determination that the rapid output increase has occurred.

12 Claims, 7 Drawing Sheets

(51) Int. Cl.
  *F01N 9/00* (2006.01)
  *F01N 11/00* (2006.01)
  *F01N 13/00* (2010.01)
  *F01N 3/023* (2006.01)
  *G01N 15/06* (2006.01)
  *F01N 3/021* (2006.01)
  *F02D 41/14* (2006.01)
  *G01N 15/00* (2006.01)
  *G01N 3/00* (2006.01)
  *G01N 15/08* (2006.01)

(52) U.S. Cl.
  CPC ............ *F01N 11/00* (2013.01); *F01N 13/008* (2013.01); *F02D 41/1494* (2013.01); *G01N 15/0656* (2013.01); *F01N 2550/04* (2013.01); *F01N 2560/05* (2013.01); *F01N 2560/12* (2013.01); *F01N 2560/20* (2013.01); *F01N 2900/0416* (2013.01); *F01N 2900/0422* (2013.01); *F01N 2900/1402* (2013.01); *F01N 2900/1606* (2013.01); *G01N 3/00* (2013.01); *G01N 15/0606* (2013.01); *G01N 2015/0046* (2013.01); *G01N 2015/084* (2013.01); *Y02T 10/47* (2013.01)

(58) Field of Classification Search
  CPC ....... F01N 2015/0046; F01N 2015/084; F01N 2550/04; F01N 2560/05; F01N 2560/12; F01N 2560/20; F01N 2900/0416; F01N 2900/0422; F01N 2900/1402; F01N 2900/1606; F02D 41/1494; F02D 41/222; G01N 15/0656; G01N 15/0606; G01N 3/00; Y02T 10/47
  USPC ........................... 60/274, 277, 295, 297, 311
  See application file for complete search history.

(56) References Cited

U.S. PATENT DOCUMENTS

| | | | |
|---|---|---|---|
| 2009/0301062 A1* | 12/2009 | Sumida | F01N 11/002 60/285 |
| 2012/0117945 A1* | 5/2012 | Krafthefer | F01N 11/00 60/274 |
| 2012/0144813 A1 | 6/2012 | Yahata et al. | |
| 2013/0204540 A1 | 8/2013 | Genssle et al. | |

* cited by examiner

APPARATUS FOR DETERMINING WHETHER THERE IS MALFUNCTION IN FILTER DEVICE

This application is the U.S. national phase of International Application No. PCT/JP2016/069526 filed 30 Jun. 2016, which designated the U.S. and claims priority to JP Patent Application No. 2015-132866 filed 1 Jul. 2015, the entire contents of each of which are hereby incorporated by reference.

TECHNICAL FIELD

The present disclosure relates to apparatuses, which are referred to as filter malfunction determination apparatuses, for determining whether there is a malfunction in a filter device, i.e. a particulate matter (PM) filter device.

BACKGROUND

A filter device is commonly disposed in the exhaust passage of an engine. The filter device is operative to collect particulate matter exhausted from the engine to thereby inhibit release of the particulate matter into the atmosphere. A PM sensor is disposed downstream from the filter device. This enables determination of whether there is a malfunction, such as a cracking failure or a melting loss, in the filter device to be carried out.

For example, a filter malfunction determination apparatus disclosed in patent literature 1 includes a pair of opposite electrodes installed to a PM sensor disposed downstream of a filter device. The filter malfunction determination apparatus uses a reduction in the resistance across the opposite electrodes due to the amount of deposited particulate matter between the opposite electrodes.

Specifically, the filter malfunction determination apparatus is adapted to determine that there is a malfunction in the filter device upon determination that the amount of the deposited particulate matter between the opposite electrodes during a predetermined malfunction determination period is equal to or more than a predetermined amount.

CITATION LIST

Patent Literature

Japanese Patent Publication No. 5115873

SUMMARY

Particulate matter may be adhered to the inner surface of the exhaust pipe of an engine and/or the filter device. In this case, if a mass of the particulate matter, i.e. a bulk of the particulate matter, is eliminated from the inner surface of the exhaust pipe and/or the filter device, and the eliminated bulk of the particulate matter is deposited between the opposite electrodes of the PM sensor, the resistance across the opposite electrodes of the PM sensor may significantly decrease. This may result in the above conventional filter malfunction determination apparatus erroneously determining that there is a malfunction in the filter device although the filter device is operating normally.

If it is determined that there is a malfunction in the filter device, a sequence of malfunction determination steps may be carried out again. In this method, a heater regeneration step is carried out such that a heater mounted to the PM sensor heats the PM sensor. After the heater regeneration step, determination of whether there is a malfunction in the filter device is carried out again. While this method prevents erroneous determination of whether there is a malfunction in the filter device, this method may unfortunately result in significantly decreasing the execution efficiency of malfunction determination of the filter device.

The present disclosure aims to solve the above issue. Specifically, the present disclosure seeks to provide filter malfunction determination apparatuses, each of which is capable of efficiently executing whether there is a malfunction in the filter device while reducing erroneous determination that there is a malfunction in the filter device.

The following describes means for solving the issue, how the means is operated, and effects obtained by the means.

A filter malfunction determination apparatus according to an exemplary aspect of the present disclosure is applied to an exhaust treatment system. The exhaust treatment system includes a filter device disposed in an exhaust pipe of an engine and configured to collect particulate matter contained in an exhaust gas of the engine. The exhaust treatment system includes a sensor disposed in the exhaust pipe downstream from the filter device and configured to output a parameter value depending on an amount of the particulate matter adhered to the sensor. The filter malfunction determination apparatus includes a malfunction determiner configured to determine whether the parameter value output from the sensor has reached a predetermined malfunction determination threshold for the filter device during a predetermined malfunction determination period, and determine that there is a malfunction in the filter device upon determination that the parameter value output from the sensor has reached the predetermined malfunction determination threshold. The filter malfunction determination apparatus includes a rapid increase determiner configured to determine whether a rapid output increase has occurred. The rapid output increase represents that an amount of increase of the parameter value per unit time output from the sensor has exceeded a predetermined value. The filter malfunction determination apparatus includes a calculator configured to calculate, upon determination that the rapid output increase has occurred, an amount of change of the parameter value output from the sensor before and after the rapid output increase. The calculator is configured to calculate, based on the calculated amount of change, a correction value for correcting at least one of the parameter value output from the sensor and the malfunction determination threshold. The filter malfunction determination apparatus includes an offset corrector configured to perform, based on the correction value, offset correction of at least one of the parameter value output from the sensor and the malfunction determination threshold after determination that the rapid output increase has occurred.

In the exhaust treatment system, if a malfunction, such as a cracking failure, has occurred in the filter device, the amount of discharge of the particulate matter toward the downstream of the filter device increases. For this reason, if the parameter value depending on the amount of the particulate matter adhered to a sensor, which is output from the sensor, has reached a malfunction determination threshold during a malfunction determination period, the filter malfunction determination apparatus determines that the filter device is malfunctioned, i.e. there is a malfunction in the filter device.

On the other hand, if the rapid output increase has occurred due to adhesion of a bulky particulate matter, which has been eliminated from an exhaust pipe or the filter device, to the sensor, the filter malfunction determination apparatus calculates, based on the amount of change of the parameter value output from the sensor before and after the rapid output increase, the correction value for correcting at least one of the parameter value output from the sensor and the malfunction determination threshold.

Then, the filter malfunction determination apparatus performs, based on the correction value, at least one of the parameter value output from the sensor and the malfunction determination threshold after determination that the rapid output increase has occurred.

The offset correction reduces erroneous determination of whether there is a malfunction in the filter device upon the occurrence of the rapid output increase. Reducing erroneous determination due to the rapid output increase enables execution of a sequence of malfunction determination steps each time of the occurrence of the rapid output increase to be eliminated. This enables the malfunction determination of the filter device to be efficiently performed while reducing erroneous determination of the filter device as having being malfunctioned.

DESCRIPTION OF THE EMBODIMENTS

Figure 1:
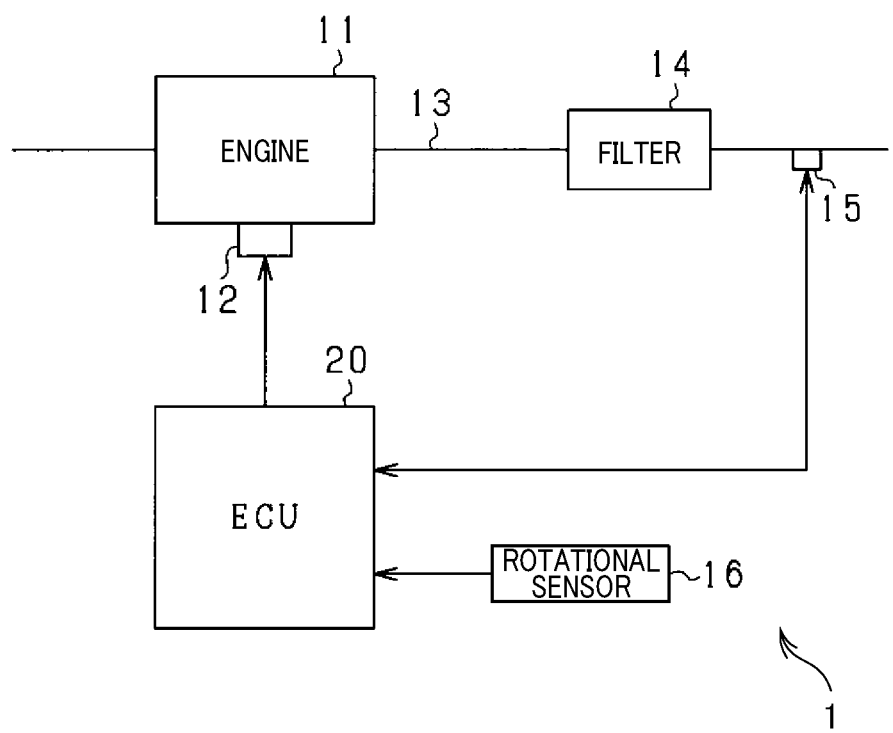
FIG. 1 is a structural view illustrating the schematic structure of an exhaust treatment system according to an embodiment of the present disclosure.

The following describes embodiments of the present disclosure with reference to the accompanying drawings. In the embodiments, like reference characters are assigned to like or identical parts between the embodiments, so that the descriptions for one of the like or identical parts are applied to another of the like or identical parts.

A filter malfunction determination apparatus 20 according to the present embodiment is for example incorporated in an exhaust treatment system 1 equipped with an engine 11; the exhaust treatment system 1 is installed in a vehicle.

The filter malfunction determination apparatus 20 includes a PM filter 14 and a PM sensor 15. The PM filter 14, which serves as a filter device, is mounted to an exhaust pipe 13 of the engine 11. The PM sensor 15 is disposed downstream from the PM filter 14, i.e. downstream in the flow of exhaust gas. The filter malfunction determination apparatus 20 is operative to monitor whether there is a malfunction in the PM filter 14 in accordance with the amount of deposited particulate matter, i.e. deposited particulates, in the PM sensor 15.

Referring to FIG. 1, the engine 11 is a diesel engine. A fuel injector 12 is provided for at least one cylinder of the engine 11; the fuel injector 12 serves as an actuator associated with the operations of the engine 11. As described above, the PM filter 14 is provided in the exhaust pipe 13 of the engine 11, and the PM sensor 15 is disposed downstream from the PM filter 14.

The exhaust treatment system 1 also includes a rotational sensor 16 and an electronic control unit (ECU) 20. The rotational sensor 16 is adapted to measure the rotational speed of the engine 11, and the ECU 20 is adapted to perform various control tasks of the engine 11. As described above, the ECU 20 serves as a filter malfunction determination apparatus 20.

The ECU 20 is for example essentially comprised of at least one microcomputer circuit 44 including, for example, a CPU, a ROM, a RAM, and other known peripheral devices. The ECU 20 runs software programs stored in, for example, the ROM to perform various tasks and/or routines. In particular, the CPU of the controller 30 runs at least one software program stored in, for example, the ROM to perform the various operation control tasks in accordance with the operating conditions of the engine 11. For example, sensors are each configured to measure a corresponding one of the operating conditions of the engine 11. The ECU 20 receives, from the sensors, signals representing operating conditions of the engine 11. Then, the ECU 20 calculates, based on the received signals, the quantity of fuel to be sprayed from the fuel injector 12 and the fuel spraying timing, and controls drive of the fuel injector 12 in accordance with the calculated quantity of fuel to be sprayed from the fuel injector 12 and the fuel spraying timing.

Figure 2:
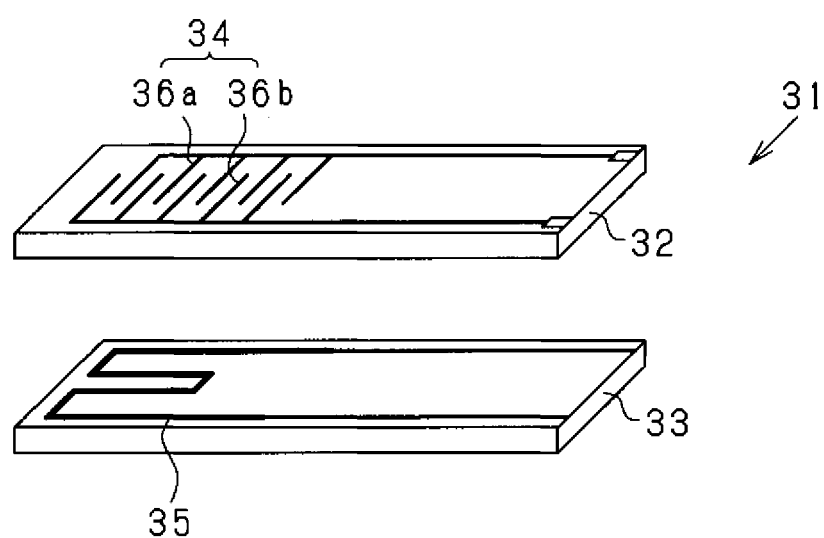
FIG. 2 is an exploded perspective view illustrating the main part of a sensor element of a PM sensor illustrated in FIG. 1 while the main part is exploded.
Figure 3:
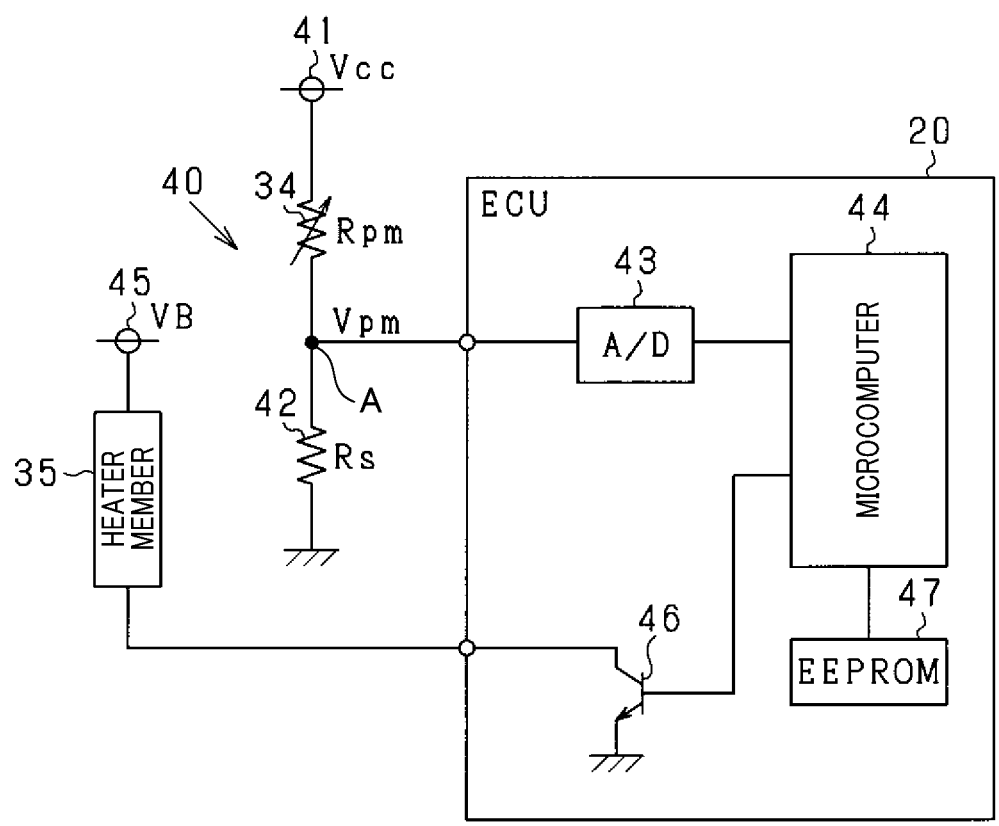
FIG. 3 is a circuit diagram illustrating the electrical configuration of each of the PM sensor and an ECU illustrated in FIG. 1.

Next, the following describes the structure of the PM sensor 15 and the electrical structure associated with the PM sensor 15 with reference to FIGS. 2 and 3.

The PM sensor 15 includes a sensor element 31.

FIG. 2 is an exploded perspective view illustrating a main part of the sensor element 31 while the main part is exploded. FIG. 3 is a circuit diagram illustrating the electrical configuration of each of the PM sensor 15 and the ECU 20.

As illustrated in FIG. 2, the sensor element 31 includes a first and second insulative substrates 32 and 33, a PM detector 34, and a heater member 35. Each of the first and second insulative substrates 32 and 33 has an elongated plate shape. The PM detector 34 is mounted to, for example, a first end of the first insulative substrate 32 in the longitudinal direction of the first insulative substrate 32. The PM detector 34 is operative to measure the amount of the particulate matter adhered to the first insulative substrate 32. The heater member 35 is mounted to the second insulative substrate 33, and operative to heat the sensor element 31. The sensor element 31 is configured such that the first and second insulative substrates 32 and 33 are stacked in the form of a bilayer.

Specifically, the first insulative substrate 32 has a first major surface and a second major surface that is opposite to the first major surface and faces the second insulative substrate 33. The first insulative substrate 32 is comprised of a pair of measurement electrodes 36a and 36b mounted on the first major surface while being spaced from each other. The pair of measurement electrodes 36a and 36b constitute the PM detector 34.

The measurement electrode 36a includes a first liner portion and a plurality of comb-tooth portions. The first liner portion is mounted on a first longitudinal edge of the first major surface, and extends linearly along the first longitudinal edge. The comb-tooth portions are mounted on the first major surface, and extend linearly from the first longitudinal edge toward the other longitudinal edge. The comb-tooth portions face each other at predetermined intervals therebetween.

Similarly, the measurement electrode 36b includes a second liner portion and a plurality of comb-tooth portions. The second liner portion is mounted on a second longitudinal edge of the first major surface, which is opposite to the first longitudinal edge. The second liner portion extends linearly along the second longitudinal edge. The comb-tooth portions are mounted on the first major surface, and extend linearly from the second longitudinal edge toward the first longitudinal edge. The comb-tooth portions face each other at predetermined intervals therebetween.

Note that the comb-tooth portions extending from the first longitudinal edge are non-contact with, i.e. spaced apart from, the second linear portion mounted on the second longitudinal edge. Similarly, the comb-tooth portions extending from the second longitudinal edge are non-contact with, i.e. spaced apart from, the first linear portion mounted on the first longitudinal edge.

The comb-tooth portions of the measurement electrode 36a and the comb-tooth portions of the measurement electrode 36b are alternately arranged to be opposite to each other along the longitudinal direction of the first major surface with predetermined spaces therebetween.

The second insulative substrate 33 has a first major surface facing the first insulative substrate 32, and a second major surface opposite to the first major surface. The second insulative substrate 33 is comprised of the heater member 35 mounted on the first major surface of the second insulative substrate 33. The heater member 35 is comprised of, for example, a heating wire.

Note that the shape of each of the measurement electrodes 36a and 36b is not limited to the above shape, each of the measurement electrodes 36a and 36b can have a desired shape. For example, each of the measurement electrodes 36a and 36b can have a curved shape. Each of the measurement electrodes 36a and 36b is comprised of an electrode portion composed of a single wire. As a pair of the measurement electrodes 36a and 36b, a pair of electrode portions can be arranged to be parallel to each other with a predetermined distance therebetween.

Note that, although illustration is omitted, the PM sensor 15 includes a holder portion for holding the sensor element 31. For example, the sensor element 31 is fixed to, for example, the inner wall of the exhaust pipe 13 while one longitudinal side of the sensor element 31 is for example held by the holder portion. In this case, the PM sensor 15 is mounted to the exhaust pipe 13 while its portion, which includes at least the PM detector 34 and the heater member 35, is arranged in the exhaust pipe 13. This arrangement of the PM sensor 15 in the exhaust pipe 13 may result in, while the exhaust gas containing the particulate matter is flowing in the exhaust pipe 13, some of the particulate matter being adhered to the measurement electrodes 36a and 36b and their peripherals of the first insulative substrate 32.

The PM sensor 15 includes a tubular insulator housing (not shown). The first end of the sensor element 31 in the longitudinal direction, to which the PM detector 34 is mounted, is located to project from the insulator housing. The PM sensor 15 also includes an unillustrated protection cover that covers the first end of the sensor element 31 in the longitudinal direction, to which the PM detector 34 is mounted.

In the PM sensor 15 configured above, adhesion of the particulate matter in the exhaust gas from the engine 11 to the first insulative substrate 32 of the sensor element 31 results in change of the resistance value of the PM detector 34, that is, change of the resistance value across the measurement electrodes 36a and 36b. Because this change of the resistance value results in change of the adhered amount of the particulate matter, the PM sensor 15 is configured to measure the adhered amount of the particulate matter using the resistance value.

As illustrated in FIG. 3, the PM sensor 15 includes, as its electrical components, the PM detector 34, a sensor power source 41, and a shunt resistor 42. The PM detector 34 serves as a variable resistor having a resistor that varies depending on change of the adhered quantity of the particulate matter. The positive end of the sensor power source 41 is connected to, for example, the measurement electrode 36a. The first end of the shut resistor 42 is connected to the measurement electrode 36b of the PM detector 34. The negative end of the sensor power source 41 is connected to the other second end of the shunt resistor 42.

The sensor power source 41 is comprised of, for example, a constant voltage circuit having a constant voltage Vcc of 5 V. The PM detector 34 and the shunt resistor 42 of the PM sensor 15 constitute a voltage divider 40. The voltage at an intermediate point A of the voltage divider 40 is input to the ECU 20 as a PM detection voltage Vpm, i.e. an output value of the PM sensor 15.

Specifically, the PM detector 34 is configured such that its resistance value Rpm changes depending on the amount of the particulate matter adhered to the PM detector 34. This change of the resistance value Rpm and a resistance value Rs of the shunt resistor 42 result in change of the output value of the PM sensor 15, i.e. the PM detection voltage Vpm. The PM detection voltage Vpm is input to the ECU 20.

Specifically, the PM detector 34 is configured to output a value of a parameter, i.e. the PM detection voltage Vpm, which changes depending on the amount of the particulate matter adhered to the PM detector 34.

The ECU 20 includes an A/D converter 43, a microcomputer 44, a transistor, i.e. an NPN transistor, 46, and an EEPROM 47, which is a nonvolatile memory.

The PM detection voltage Vpm is converted by the A/D converter 43 into digital data. The PM detection voltage Vpm, which was converted into the digital data, is input to the microcomputer 44. The microcomputer 44 calculates the quantity of the particulate matter (PM) adhered to the PM sensor 15 in accordance with the PM detection voltage Vpm input thereto.

The heater member 35 of the PM sensor 15 includes a first high-voltage end, a second constant-voltage end opposite thereto. The heater power source 45 is connected to the first high-voltage end. The heater power source 45 is for example a battery installed in the corresponding vehicle, and the heater member 35 is configured to be heated when energized by the heater power source 45. The second constant-voltage end is connected to the ground via an input terminal, i.e. the collector, of the transistor 46 of the ECU 20. The transistor 46 has a control terminal, such as the base, connected to the microcomputer 44.

Specifically, the heater member 35 is configured to not be heated upon the microcomputer 44 controlling the transistor 46 to be off, because no current flows from the heater power source 45 into the ground via the heater member 35. Otherwise, the heater member 35 is configured to be heated upon the microcomputer 44 sending a control signal to the control terminal of the transistor 46 to turn on the transistor 46, because a current flows from the heater power source 45 into the ground via the heater member 35.

Specifically, the microcomputer 44 controls on-off switching operations of the transistor 46 to thereby perform heating control of the heater member 35, i.e. perform control of, for example, the heating timing and heating period of the heater member 35.

Start of energization of the heater member 35 by the microcomputer 44 while the particulate matter is adhered to the first insulative substrate 32 results in an increase of the temperature of the adhered particulate matter, resulting in the adhered particulate matter being forcibly heated. This forcible heating eliminates the particulate matter adhered to the first insulative substrate 32. The microcomputer 44 determines that a forcible heating request has occurred after start-up of the engine 11 or after termination of the engine 11, and performs the heating control of the heater member 35 based on control of the transistor 46, thus performing a forcible heating task of the particulate matter of the PM sensor 15.

Note that the forcible heating task of the particulate matter of the PM sensor 15 is called a sensor regeneration task, because the forcible heating task regenerates the function of the PM sensor 15 for detecting the adhered amount of the particulate matter in the PM sensor 15.

The EEPROM 47 serves as a backup memory for storing various learning values and malfunction diagnostic values, i.e. diagnostic data values.

The ECU 20 executes a malfunction determination routine of the PM filter 14, i.e. a filter malfunction determination routine, in accordance with the PM detection voltage Vpm.

Specifically, the ECU 20 performs the malfunction determination routine of the PM filter 14 during a predetermined malfunction determination period after start-up of the engine 11. The malfunction determination routine of the PM filter 14 means a routine for determining whether a malfunction, such as a cracking failure or a melting loss, has occurred in the PM filter 14 in accordance with whether the adhered amount of the particulate matter in the PM filter 14 has exceeded a malfunction determination threshold Th1.

The ECU 20 according to the present embodiment performs an initial sensor regeneration task, i.e. an early-stage regeneration task. Then, the ECU 20 performs the malfunction determination routine of the PM filter 14 during a predetermined time after completion of the initial sensor regeneration task; the predetermined time after completion of the initial sensor regeneration task is defined as the malfunction determination period. Note that the predetermined time can be set to, for example, 20 minutes.

The particulate matter may be adhered to the inner surface of the exhaust pipe 13 and/or the PM filter 14. In this case, if a mass of the particulate matter, i.e. a bulk of the particulate matter, is eliminated to be deposited between the electrodes of the PM sensor 15, the PM detection voltage 15 may significantly increase. This may result in the amount of the deposited particulate matter having exceeded the malfunction determination threshold Th1. This may result in the ECU 20 erroneously determining that there is a malfunction in the PM filter 14 although the PM filter 14 is operating normally. If it is determined that there is a malfunction in the PM filter 14, execution of the sensor regeneration task by the ECU 20 using the heating of the heater member 35 may unfortunately result in significantly decreasing in execution efficiency of the malfunction determination routine by the ECU 20.

From this viewpoint, the ECU 20 according to the present embodiment performs offset correction of the PM detection voltage Vpm upon determining that the PM detection voltage Vpm has increased rapidly due to deposit of the bulk particulate matter to the PM sensor 15. This offset correction is configured to offset the PM detection voltage Vpm to be lower to thereby inhibit the PM detection voltage Vpm from exceeding the malfunction determination threshold Th1. This prevents erroneous determination of whether the PM filter 14 is operating normally or abnormally.

The ECU 20 also performs offset correction of the PM detection voltage Vpm upon determining that the PM detection voltage Vpm had decreased rapidly due to elimination of a mass of the particulate matter from the PM sensor 15. This offset correction is configured to offset the PM detection voltage Vpm to be higher to thereby accurately know the amount of discharge of the particulate matter from the PM filter 14. This prevents erroneous determination of whether the PM filter 14 is operating normally or abnormally.

Figure 4:
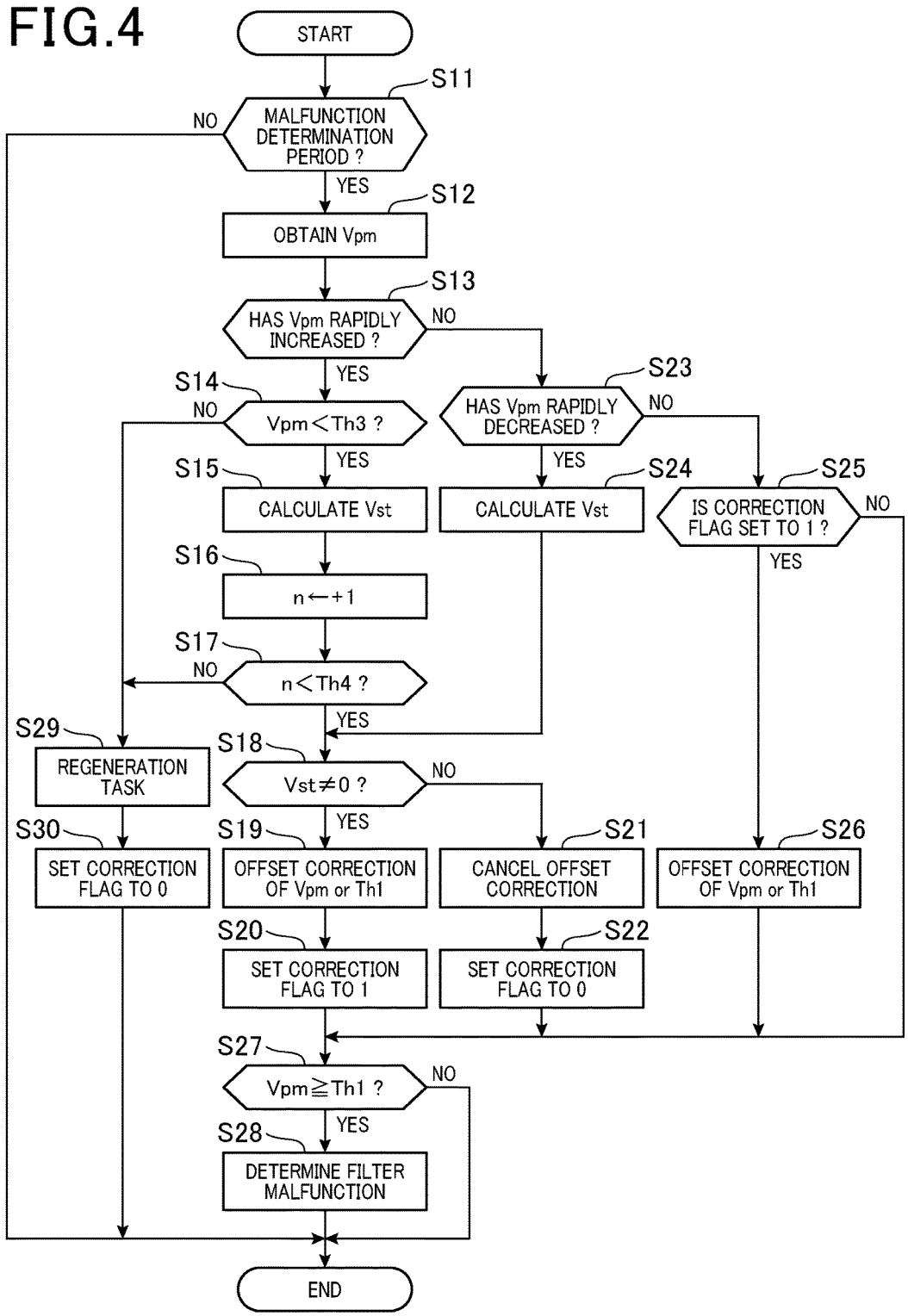
FIG. 4 is a flowchart schematically illustrating a filter malfunction determination routine carried out by the ECU illustrated in FIG. 1.

Next, the following describes the filter malfunction determination routine carried out by the ECU 20 with reference to the flowchart of FIG. 4. This routine is carried out by the ECU 20, i.e. the microcomputer 44 repeatedly in a predetermined period.

First, in step S11, the microcomputer 44 determines whether it is time to the filter malfunction determination routine during the malfunction determination period of the PM filter 14. Upon determination being NO in step S11, the microcomputer 44 terminates the filter malfunction determination routine. Otherwise, upon determination being YES in step S11, the filter malfunction determination routine proceeds to step S12. In step S12, the microcomputer 44 obtains, via the A/D converter 43, the PM detection voltage Vpm.

In step S13, the microcomputer 44 determines whether the PM detection voltage Vpm has increased rapidly. As an example of determination of whether the PM detection voltage Vpm has increased rapidly, the microcomputer 44 determines, for example, whether the amount of change of the PM detection voltage Vpm per unit of time is larger than a threshold Th2.

Specifically, the microcomputer 44 calculates the difference of the value in the last previous cycle of the filter malfunction determination routine from the value of the PM detection voltage Vpm in the current cycle of the filter malfunction determination routine. Then, the microcomputer 44 determines whether the difference is larger than the threshold Th2. Note that the threshold Th2 is preferably set to be larger than the amount of change of the PM detection voltage Vpm estimated based on the discharge through the PM filter 14 during the actual operating state of the engine 11. The threshold Th2 can be set assuming that there is a cracking failure or a melting loss in the PM filter 14 or the exhaust gas from the engine 11 is directly transferred to the PM sensor 15.

Upon a YES determination in step S13, the filter malfunction determination routine proceeds to step S14. In step S14, the microcomputer 44 determines whether the value of the PM detection voltage Vpm, which has increased rapidly, is smaller than an acceptable value Th3. Note that the acceptable value Th3 is set to a predetermined value. For example, the acceptable value Th3 is preferably set to a value larger than the malfunction determination threshold Th1. Of course, the acceptable value Th3 can be set to be smaller than the malfunction determination threshold Th1.

Upon a YES determination in step S14, the filter malfunction determination routine proceeds to step S15. In step S15, the microcomputer 44 calculates a correction value Vst based on a change amount ΔVpm before and after the rapid increase of the PM detection voltage Vpm; the correction value Vst aims to correct the PM detection voltage Vpm.

Specifically, the microcomputer 44 calculates the change amount ΔVpm between a value Vpm1 and a value Vpm2; the value Vpm1 represents a value of the PM detection voltage Vpm being stable before its rapid increase, and the value Vpm2 represents a value of the PM detection voltage Vpm being stable after its rapid increase, which is for example expressed by the following equation:

$$Vst=\Delta Vpm=Vpm2-Vpm1$$

Then, the microcomputer 44 regards the change amount ΔVpm as the correction value Vst.

At that time, in step S15, as to a rapid increase of the PM detection voltage Vpm for the second or subsequent times, the microcomputer 44 adds the change amount ΔVpm obtained at the current rapid increase to the change amount ΔVpm obtained at the last previous rapid increase to correspondingly calculate the correction value Vst. That is, assuming that the rapid increase at a current time is referred to as the rapid increase at the x time (x is an integer equal to or more than 2), the microcomputer 44 calculates a correction value Vst(x) for the rapid increase at the current x time in accordance with the following equation:

$$Vst(x)=Vst(x-1)+\Delta Vpm \qquad (1)$$

In step S16, the microcomputer 44 increments the number n of rapid increase of the PM detection voltage Vpm by 1. In the subsequent step S17, the microcomputer 44 determines whether the number of rapid increases of the PM detection voltage Vpm is smaller than a predetermined number Th4. Note that the predetermined number Th4 is set to a predetermined value of, for example, 3.

Upon affirmative determination in step S17, the filter malfunction determination routine proceeds to step S18. In step S18, the microcomputer 44 determines whether the correction value Vst is a value other than zero. Upon a YES determination in step S18, the microcomputer 44 performs offset correction of the PM detection voltage Vpm, thus offsetting, based on the correction value Vst, the PM detection value Vpm to be lower.

Specifically, the microcomputer 44 calculates an offset-corrected PM detection voltage Vpmc in accordance with the following equation (1):

$$Vpmc=Vpm-Vst \qquad (1)$$

In step S20, the microcomputer 44 sets an offset correction flag to 1. The offset correction flag is a variable. When being set to 0, the variable represents that the correction value Vst is 0, that is, represents the state where offset correction is not being performed for the PM detection voltage Vpm. Otherwise, when being set to 1, the variable represents that the correction value Vst is other than 0, that is, represents the state where offset correction is being performed for the PM detection voltage Vpm.

Otherwise, upon a NO determination in step S13, that is, upon determination that the obtained PM detection voltage has not increased rapidly, the microcomputer 44 determines whether the PM detection voltage Vpm has decreased rapidly in step S23. As an example of determination of whether the PM detection voltage Vpm has decreased rapidly, the microcomputer 44 determines, for example, whether the amount of change of the PM detection voltage Vpm per unit of time is larger than a threshold Th5. Note that the threshold Th2 for determination of rapid increase of the PM detection voltage Vpm and the threshold Th5 for determination of rapid decrease of the PM detection voltage Vpm can be set to be equal to each other, or set to be different from each other.

Specifically, the microcomputer 44 calculates the difference of the value in the last previous cycle of the filter malfunction determination routine from the value of the PM detection voltage Vpm in the current cycle of the filter malfunction determination routine. Then, the microcomputer 44 determines whether the difference is a negative value and the absolute value of the difference is larger than the threshold Th5.

Upon a YES determination in step S23, the microcomputer 44 changes the correction value Vst at the affirmative determination in step S23 in accordance with the correction amount ΔVpm before and after the rapid increase of the PM detection voltage Vpm in step S24.

That is, similar to the case of the rapid increase of the PM detection voltage Vpm, the microcomputer 44 calculates the change amount ΔVpm, which is a negative value, between a value Vpm1 and a value Vpm2; the value Vpm1 represents a value of the PM detection voltage Vpm being stable before its rapid decrease, and the value Vpm2 represents a value of the PM detection voltage Vpm being stable after its rapid decrease, which is for example expressed by the following equation:

$$Vst=\Delta Vpm=Vpm2-Vpm1$$

Similar to the case of the rapid increase of the PM detection voltage Vpm, as to a rapid decrease of the PM detection voltage Vpm for the second or subsequent times, the microcomputer 44 calculates, assuming that the rapid decrease at a current time is referred to as the rapid decrease at the x time (x is an integer equal to or more than 2), a correction value Vst(x) for the rapid decrease at the current x time in accordance with the following equation:

$$Vst(x)=Vst(x-1)+\Delta Vpm \qquad (2)$$

Note that, similar to the first rapid increase, as to the first rapid decrease, the microcomputer 44 calculates the change amount ΔVpm based on the equation ΔVpm=Vpm2−Vpm1, thus regarding the change amount ΔVpm as the correction voltage Vst, which is expressed by the following equation Vst=ΔVpm=Vpm2−Vpm1. Because the change amount ΔVpm is a negative value during rapid decrease of the PM detection voltage Vpm, the correction value Vst becomes a negative value.

For the rapid decrease of the PM detection voltage Vpm, the microcomputer 44 adds the negative change amount ΔVpm to the last previous correction value Vst to thereby calculate the correction value Vst.

Figure 5:
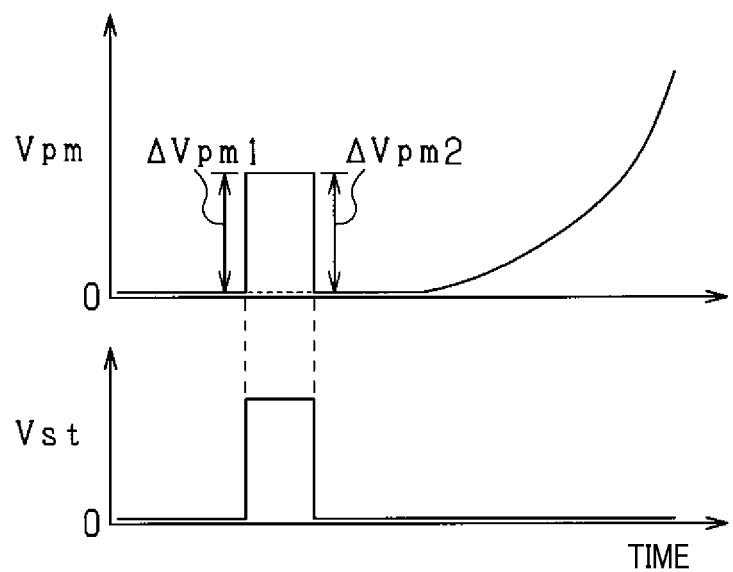
FIG. 5 is a timing chart illustrating an example of offset correction of a PM detection voltage.
Figure 6:
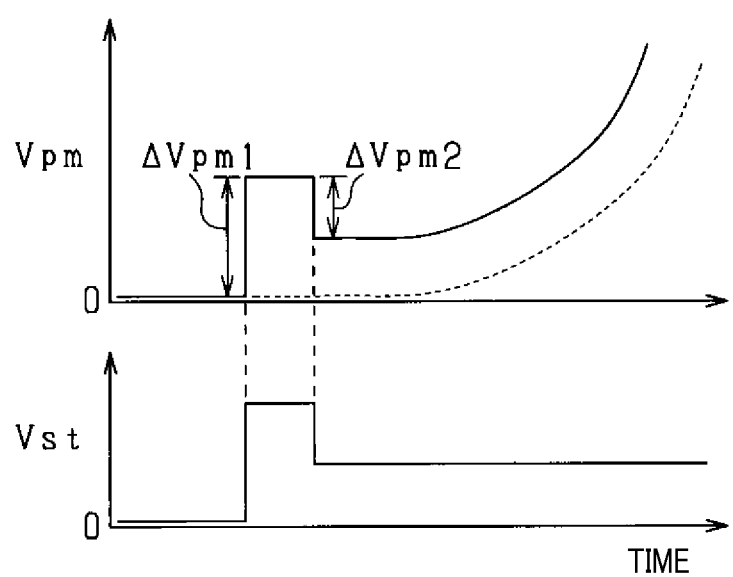
FIG. 6 is a timing chart illustrating another example of the offset correction of the PM detection voltage.

The following describes how the correction value Vst is calculated for the rapid decrease of the PM detection voltage Vpm with reference to FIGS. 5 and 6. Note that each of FIGS. 5 and 6 is a timing chart illustrating offset correction of the PM detection voltage Vpm. In each of FIGS. 5 and 6, the solid line represents the PM detection voltage Vpm, and the dashed line represents the offset-corrected PM detection voltage Vpmc.

FIG. 5 shows a case where the change amount ΔVpm1 before and after a rapid increase of the PM detection voltage Vpm is identical to the change amount ΔVpm2 before and after a rapid decrease of the PM detection voltage Vpm. For example, this case is estimated as a case where a bulk of the particulate matter, which has been adhered to the PM sensor 15, is completely eliminated from the PM sensor 15. In this case, the microcomputer 44 sets the change amount ΔVpm1 as the correction value Vst before and after the rapid increase of the PM detection voltage Vpm, and changes the correction value Vst to zero based on the change amount ΔVpm2 as the correction value Vst before and after the rapid decrease of the PM detection voltage Vpm.

That is, the microcomputer 44 calculates the correction value Vst during the rapid decrease of the PM detection voltage Vpm in accordance with the following equation (3):

$$Vst = \Delta Vpm2 - \Delta Vpm1 \qquad (3)$$

This results in the correction value Vst being zero upon the change amount ΔVpm1 before and after the rapid increase of the PM detection voltage Vpm being identical to the change amount ΔVpm2 before and after the rapid decrease of the PM detection voltage Vpm.

FIG. 6 shows a case where the change amount ΔVpm2 before and after a rapid decrease of the PM detection voltage Vpm is smaller than the change amount ΔVpm1 before and after a rapid increase of the PM detection voltage Vpm. For example, this case is estimated as a case where a bulk of the particulate matter, which has been adhered to the PM sensor 15, is partly eliminated from the PM sensor 15, so that the remainder of the bulky particulate matter remains adhered to the PM sensor 15. In this case, because the absolute value of the change amount ΔVpm2 before and after the rapid decrease of the PM detection voltage Vpm is smaller than the absolute value of the change amount ΔVpm1 before and after the rapid increase of the PM detection voltage Vpm, the microcomputer 44 changes the correction value Vst in accordance with the difference "ΔVpm2−ΔVpm1". This enables the discharge amount of the particulate matter from the PM filter 14 to be accurately obtained even if the PM detection voltage Vpm has increased based on the remainder of the bulky particulate matter adhered to the PM sensor 15.

Returning to FIG. 4, in step S18, the microcomputer 44 determines whether the correction value Vst is a value other than zero. Upon a YES determination in step S18, the microcomputer 44 performs offset correction of the PM detection voltage Vpm based on the correction value Vst in step S19. That is, upon a YES determination in step S23, i.e. upon determination that the PM detection voltage Vpm has decreased rapidly, the microcomputer 44 performs offset correction of the PM detection voltage Vpm, thus offsetting, based on the correction value Vst, the PM detection value Vpm to be higher.

Specifically, the microcomputer 44 calculates the offset-corrected PM detection voltage Vpmc in accordance with the following equation (4):

$$Vpmc = Vpm - Vst \qquad (4)$$

As described above, because the correction value Vst is a negative value, the equation (4) shows offset correction of the PM detection voltage Vpm to be higher.

In the subsequent step S20, the microcomputer 44 sets the offset correction flag to 1.

Otherwise, upon a NO determination in step S18, the microcomputer 44 cancels the offset correction of the PM detection voltage Vpm in step S21, and sets the offset correction flag to 0 in step S22.

Otherwise, upon a NO determination in step S23, the microcomputer 44 determines whether the offset flag has been set to 1 in step S25. Upon a YES determination in step S25, the microcomputer 44 for example carries out the offset correction of the PM detection voltage Vpm, which is the same as the offset correction of the PM detection voltage Vpm carried out in the last previous filter malfunction determination routine.

After negative determination in step S25, or after the operation in step S20, S22, or S26, the microcomputer 44 determines whether the PM detection voltage Vpm or the corrected PM detection voltage Vpmc is equal to or more than the malfunction determination threshold Th1 in step S27.

Upon a NO determination in step S27, the microcomputer 44 terminates the filter malfunction determination routine. In contrast, upon a YES determination in step S28, the microcomputer 44 determines that a malfunction has occurred in the PM filter 14, and thereafter, terminates the filter malfunction determination routine.

On the other hand, upon a NO determination in any one of steps S14 and S17, the microcomputer 44 performs the sensor generation task of the PM sensor 15 described above.

Specifically, if the PM detection voltage Vpm, which has increased rapidly, becomes equal to or higher than the acceptable value Th3 or the number of rapid increases of the PM detection voltage Vpm has exceeded the acceptable number Th4, masses of the bulky particulate matter are estimated to have been adhered to the PM sensor 15. This may result in reduction of the reliability of the malfunction determination. For this reason, execution of the sensor regeneration task enables the particulate matter to be heated, resulting in the particulate matter being eliminated.

After the operation in step S29, the microcomputer 44 sets the offset correction flag to 0 in step S30, and thereafter, the microcomputer 44 terminates the filter malfunction determination routine.

Figure 7:
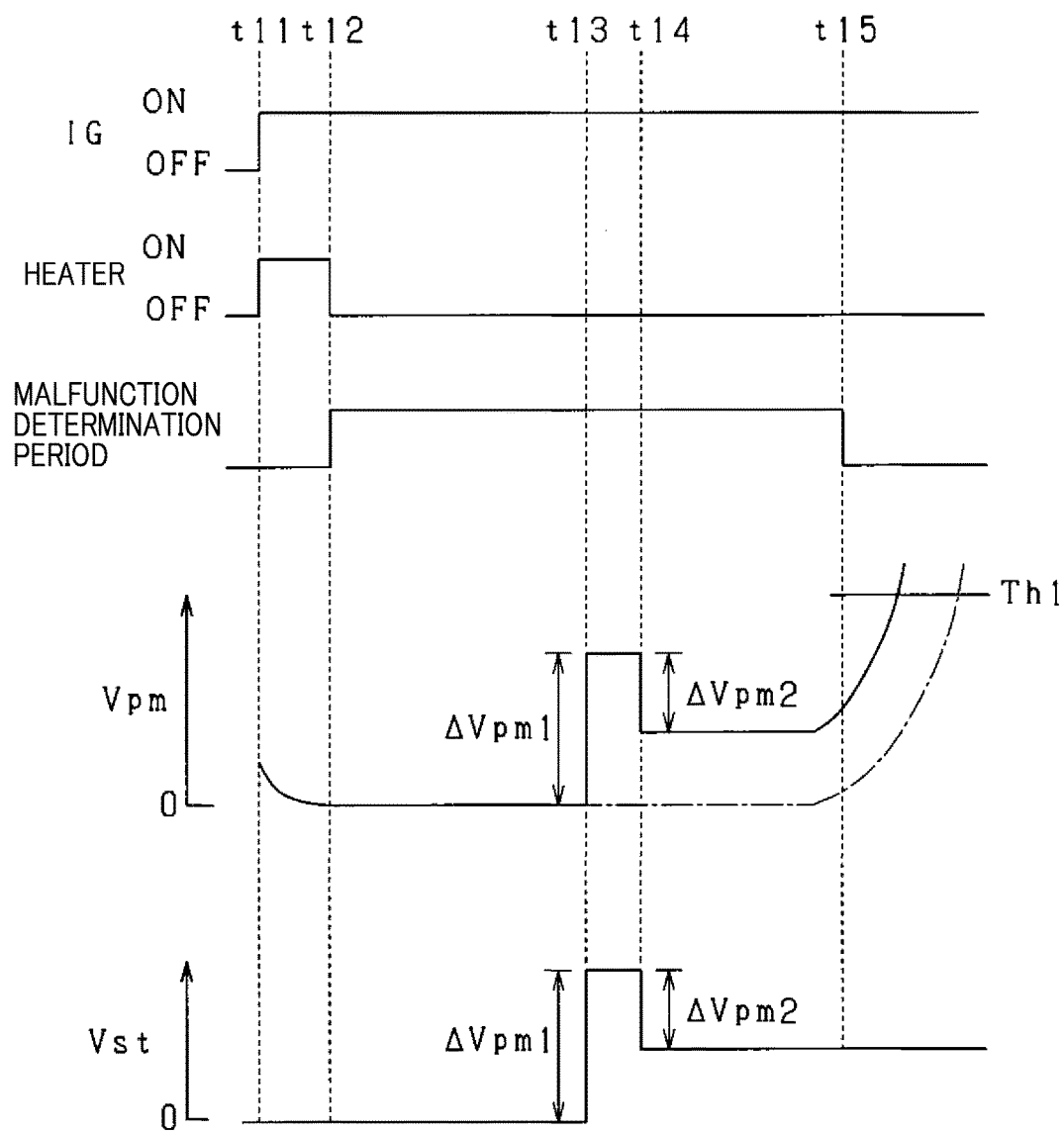
FIG. 7 is a timing chart schematically illustrating how the PM detection voltage and a corrected voltage are changed based on execution of the filter malfunction determination routine.

Next, the following describes how the PM detection voltage Vpm and the correction value Vst are changed based on execution of the filter malfunction determination routine using the flowchart of FIG. 7. It is assumed that the timing chart of FIG. 7 is carried out immediately after start-up of the engine 11 in response to the switching pf an ignition switch (IG) from off to on.

At time t11 after turn-on of the IG switch, energization of the heater member 35 is started as the initial regeneration task (OFF→ON in FIG. 7). Energization of the heater member 35 eliminates the particulate matter adhered to the PM sensor 15 immediately after the start-up of the engine 11.

At time t12 when a predetermined delay time has elapsed since the PM detection voltage Vpm fallen down to 0 V based on the initial regeneration task, energization of the heater member 35 is terminated, so that the temperature of the PM sensor 15 decreases. After the temperature of the PM sensor 15 has decreased down to a predetermined temperature, the malfunction determination of the PM filter 14 is started.

Upon determination that a bulk of the particulate matter has been adhered to the PM sensor 15 so that the PM detection voltage Vpm has increased rapidly at time t13, the change amount ΔVpm1 before and after the rapid increase of the PM detection voltage Vpm is calculated, and the calculated PM detection voltage Vpm is set as the correction value Vst. Thereafter, offset correction of the PM detection voltage Vpm is carried out based on the correction value Vst, so that the offset-corrected Vpmc is maintained without increasing rapidly.

At time t14 when the bulky particulate matter is eliminated from the PM sensor 15, so that it is determined that the PM detection voltage Vpm has decreased rapidly, the correction value Vst at the time t14 is changed depending on the change amount ΔVpm2 before and after the rapid decrease of the PM detection voltage Vpm. After the time t14, offset correction of the PM detection voltage Vpm is carried out based on the changed correction value Vst.

Thereafter, the predetermined malfunction determination period has ended at time t15. At the time t15, upon determination that the PM detection voltage Vpm being lower than the malfunction determination threshold Tth1, it is determined that the PM filter 14 is operating normally.

As described in detail above, the exhaust treatment system 1, i.e. the filter malfunction determination apparatus 20 constituting the ECU 20, obtains the following superior advantageous effects.

If the PM detection voltage has increased rapidly due to adhesion of a bulk of the particulate matter, which has escaped from the exhaust pipe 13 or the PM filter 14, to the PM sensor 15, the above filter malfunction determination apparatus 20 calculates the correction value Vst for correcting the PM detection voltage Vpm in accordance with the change value ΔVpm before and after the rapid increase of the PM detection voltage Vpm. After determination that the PM detection voltage Vpm has increased rapidly, the filter malfunction determination apparatus 20 performs offset correction of the PM detection voltage Vpm as a function of the correction value Vst.

For this reason, the filter malfunction determination apparatus 20 configured above inhibits erroneous determination of the PM filter 14 being malfunctioned when the PM detection voltage Vpm has increased rapidly. The filter malfunction determination apparatus 20 configured above enables execution of a sequence of malfunction determination steps each time the PM detection voltage Vpm rapidly increases to be eliminated. This enables the malfunction determination routine of the PM filter 14 to be efficiently performed while inhibiting erroneous determination of the PM filter 14 being malfunctioned.

The filter malfunction determination apparatus 20 is configured to, upon rapid decrease of the PM detection voltage Vpm due to elimination of the bulky particulate matter from the PM sensor 15, change the correction value Vst at the time of the rapid decrease of the PM detection voltage Vpm in accordance with the change amount ΔVpm before and after of the PM detection voltage Vpm. This configuration enables, upon rapid decrease of the PM detection voltage Vpm in addition to rapid increase of the PM detection voltage Vpm, the correction value Vst depending on the rapid decrease of the PM detection voltage Vpm to be calculated. For this reason, the filter malfunction determination apparatus 20 enables the amount of discharge of the particulate matter from the PM filter 14 to be accurately checked even in the occurrence of rapid increase or rapid decrease of the PM detection voltage Vpm during the malfunction determination period.

The filter malfunction determination apparatus 20 is configured to calculate the correction value Vst as a function of the difference between (1) The change amount ΔVpm1 before and after the rapid increase of the PM detection voltage Vpm (2) The change amount ΔVpm2 before and after the rapid decrease of the PM detection voltage Vpm This configuration reduces the possibility of the PM filter 14 being determined to be malfunctioned even if the PM detection voltage has increased due to the remainder of a bulk of the particulate matter.

The filter malfunction determination apparatus 20 is configured to perform the sensor regeneration task upon determination that the PM detection voltage Vpm after a rapid increase of the PM detection voltage Vpm is equal to or more than the acceptable value Th3 or the number n of rapid increase of the PM detection voltage Vpm has reached the predetermined number Th4. This configuration enables masses of the bulky particulate matter to be thermally eliminated; the masses of the bulky particulate matter are a factor causing decreased reliability of the malfunction determination routine. The sensor regeneration task carried out to avoid reduction of the reliability of the malfunction determination routine due to the masses of the bulky particulate matter enables the reliability of the malfunction determination routine of whether the PM filter 14 has malfunctioned to be maintained at a higher level.

Other Embodiments

The above embodiment can be modified as follows.

The microcomputer 44 can be modified to clear the correction value Vst to zero upon the PM detection voltage Vpm rapidly decreasing to be equal to or less than a predetermined low voltage threshold Th6.

Figure 8:
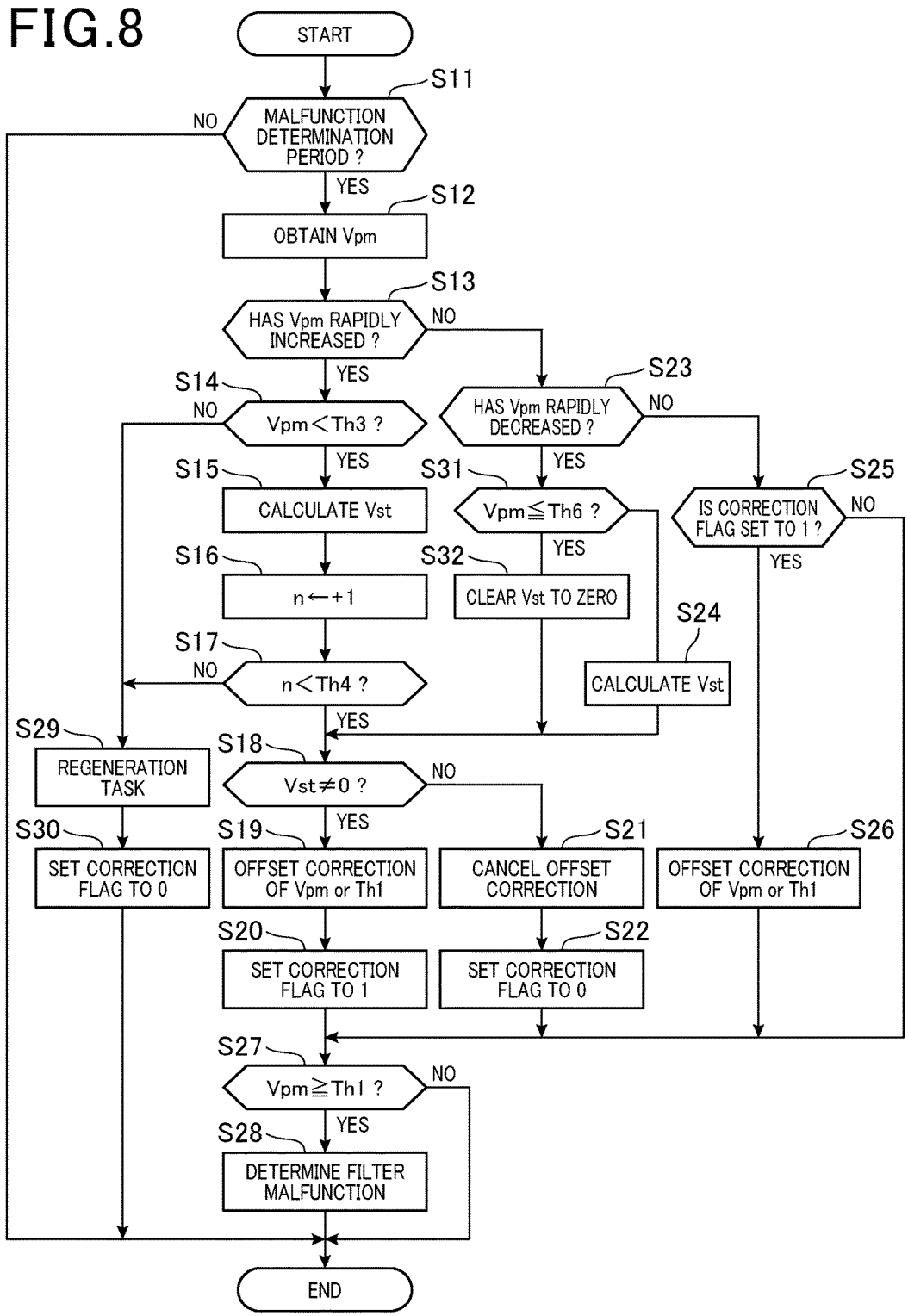
FIG. 8 is a flowchart schematically illustrating a filter malfunction determination routine according to a modification of the embodiment of the embodiment of the present disclosure.

The following describes the filter malfunction determination routine carried out by the ECU 20, i.e. the microcomputer 44, according to this modification using the flowchart of FIG. 8. This filter malfunction determination routine is carried out in place of the routine illustrated in FIG. 4. In FIG. 8, operations in some steps whose step numbers are assigned to the corresponding equivalent steps in FIG. 4 are omitted.

Specifically, the filter malfunction determination routine according to the modified embodiment further includes the operations in steps S31 and S32 in addition to the filter malfunction determination routine illustrated in FIG. 4.

Upon determination that the PM detection voltage Vpm has rapidly decreased during the malfunction determination period in step S11 to S13 and S23, the microcomputer 44 determines whether the PM detection voltage Vpm, which has decreased rapidly, is equal to or less than the predetermined low threshold Th6 in step S31.

Upon a YES determination in step S31, the microcomputer 44 clears the correction value Vst to zero in step S32. Then, the filter malfunction determination routine proceeds to step S18.

Upon determination that the correction value Vst is zero in step S18, and the offset correction of the PM detection voltage Vpm is cancelled in step S21, the microcomputer 4 resets the offset correction flag to zero.

The following describes how the PM detection voltage Vpm is changed if the offset correction of the PM detection voltage Vpm, which has decreased rapidly to be equal to or lower than the predetermined low voltage threshold Th6, is cancelled.

Figure 9:
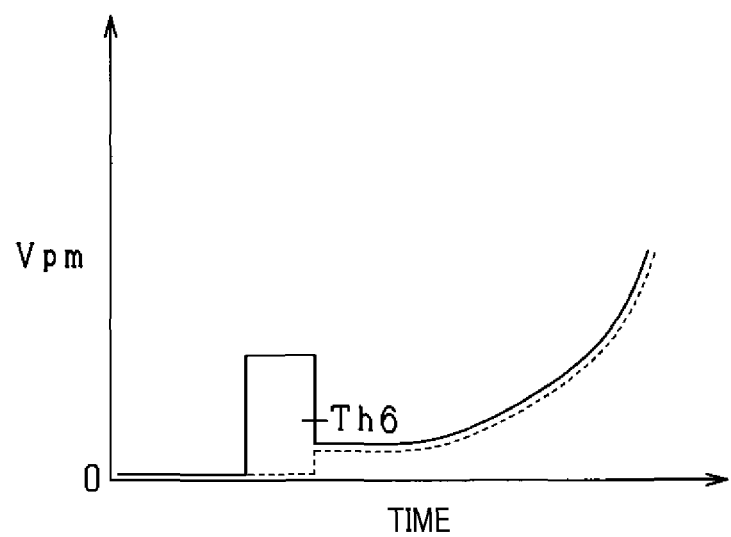
FIG. 9 is a timing chart schematically illustrating how the PM detection voltage is changed according to the modified embodiment.

Note that FIG. 9 illustrates the PM detection voltage Vpm is changed during the malfunction determination period. Specifically, the solid curve in FIG. 9 represents the output values of the PM detection voltage Vpm during the malfunction determination period according to this modified example where the PM detection voltage Vpm to which no offset correction is applied.

In contrast, the dashed curve in FIG. 9 represents the output values of the PM detection voltage Vpm during the malfunction determination period according to this modified example where the PM detection voltage Vpm has had the offset correction applied.

FIG. 9 shows an example whether the PM detection voltage Vpm, which has decreased rapidly, is equal to or less than the predetermined low voltage threshold Vth6. This is estimated under the situation where a part of the particulate matter remains to be adhered to the PM sensor 15. This may be due to the remainder of the particulate matter, which were discharged from the PM filter 14, adhered to the PM sensor 15 during, for example, the period from the rapid increase of the PM detection voltage Vpm to the rapid decrease of the PM detection voltage Vpm. In this modified embodiment, cancelling the offset correction prevents execution of unnecessary offset correction for an increase of the PM detection voltage Vpm due to some particulates discharged through the PM filter 14.

Otherwise, upon a NO determination in step S31, the microcomputer 44 calculates, based on the change amount ΔVpm before and after a rapid decrease of the PM detection voltage Vpm, the correction value Vst for correcting the PM detection voltage Vpm in step S24, and thereafter, carries out the operation in step S18. In steps S18 to S20, the microcomputer 44 determines whether the correction value Vst is a value other than zero, and performs offset correction of the PM detection voltage Vpm upon determination that the correction value Vst is a value other than zero.

The above configuration of this modified example enables execution of unnecessary offset correction to be prevented in a case where the PM detection voltage Vpm, which has decreased rapidly, becomes equal to or lower than the predetermined low voltage threshold Th6. This therefore makes it possible to properly determine whether to perform offset correction of the PM detection voltage Vpm in accordance with how the particulate matter is adhered to the PM sensor 15.

The low voltage threshold Th6 is set to a predetermined value, but the microcomputer 44 can variably set the low voltage threshold Th6 to any value. In this modification, the microcomputer 44 for example can set the low voltage threshold Th6 to be larger as a value of the PM detection voltage Vpm immediately before its rapid decrease is larger than a value of the PM detection voltage Vpm immediately after its rapid increase.

The microcomputer 44 according to the present embodiment is configured to perform offset correction of the output value of the PM detection voltage Vpm, but the present disclosure is not limited to this configuration. Specifically, the microcomputer 44 can be configured to perform offset correction of the malfunction determination threshold Th1.

In this modification, upon determination that the PM detection voltage Vpm has increased rapidly (YES in step S13) and the a YES determination in step S14 is YES, the microcomputer 44 calculates the change amount ΔVpm before and after the rapid increase of the PM detection voltage Vpm set forth above (see step S15). Then, upon determination that the determination of each of steps S17 and S18 is affirmative, the microcomputer 44 performs offset correction of the malfunction determination threshold Th1 using the change amount ΔVpm as the correction value Vst to thereby offset the malfunction determination threshold Th1 to be higher in step S19.

Specifically, the microcomputer 44 calculates a corrected malfunction determination threshold in accordance with the following equation (5):

$$Th1c = Th1 + Vst \tag{5}$$

Where Th1c represents the corrected malfunction determination threshold.

Upon determination that the PM detection voltage Vpm has decreased rapidly (YES in step S23), the microcomputer 44 calculates, for example, the difference of the change amount ΔVpm before and after the rapid increase of the PM detection voltage Vpm from the change amount ΔVpm before and after the rapid decrease of the PM detection voltage Vpm. Then, the microcomputer 44 performs offset correction of the malfunction determination threshold Th1 using the calculated difference as the correction value Vst to thereby offset the malfunction determination threshold Th1 to be lower in step S19.

Specifically, the microcomputer 44 calculates the corrected malfunction determination threshold Th1c in accordance with the following equation (6):

$$Th1c = Th1c + Vst \tag{6}$$

As described above, because the correction value Vst is a negative value, the equation (6) represents offset correcting the malfunction determination threshold Th1c, i.e. offsetting the malfunction determination threshold Th1c to be lower.

The predetermined time after completion of the initial sensor regeneration task of the engine 11 is defined as the malfunction determination period, but the malfunction determination period can be freely set. For example, the ECU 20 can be configured to perform the sensor regeneration task during the engine 11 operating, and the malfunction determination period can be set after completion of the sensor regeneration task.

This application is based on and claims the benefit of priority from Japanese Patent Application 2015-132866, the disclosure of which is incorporated in its entirety herein by reference.

REFERENCE SIGNS LIST

1 Exhaust treatment system
11 Engine
13 Exhaust pipe
14 PM filter (Filter device)
15 PM sensor
20 ECU (Filter malfunction determination apparatus)

The invention claimed is:

1. A filter malfunction determination apparatus applied to an exhaust treatment system comprising a filter device disposed in an exhaust pipe of an engine and configured to collect particulate matter contained in an exhaust gas of the engine; and a sensor disposed in the exhaust pipe downstream from the filter device and configured to output a parameter value depending on an amount of the particulate matter adhered to the sensor, the filter malfunction determination apparatus comprising:

an electronic control unit, including a computer processor, the electronic control unit at least configured to:

determine whether the parameter value output from the sensor has reached a predetermined malfunction determination threshold for the filter device during a predetermined malfunction determination period;

determine that there is a malfunction in the filter device upon determination that the parameter value output from the sensor has reached the predetermined malfunction determination threshold;

determine whether a rapid output increase has occurred, the rapid output increase representing that an amount of increase of the parameter value per unit time output from the sensor has exceeded a predetermined value;

calculate, upon determination that the rapid output increase has occurred, an amount of change of the parameter value output from the sensor before and after the rapid output increase;

calculate, based on the calculated amount of change, a correction value for correcting at least one of the parameter value output from the sensor and the malfunction determination threshold; and perform, based on the correction value, offset correction of at least one of the parameter value output from the sensor and the malfunction determination threshold after determination that the rapid output increase has occurred.

2. The filter malfunction determination apparatus according to claim 1, wherein the electronic control unit is further configured to determine whether a rapid output decrease has occurred after determination that the rapid output increase has occurred, the rapid output decrease representing that an amount of decrease of the parameter value per unit time output from the sensor has exceeded a prescribed value, calculate, upon determination that the rapid determination decrease has occurred, calculate a change quantity of the parameter value output from the sensor before and after the rapid output decrease; and correct, based on the change quantity, the correction value at the determination of the rapid output decrease.

3. The filter malfunction determination apparatus according to claim 2, wherein:

the electronic control unit is further configured to calculate the correction value in accordance with a difference between the change amount before and after the rapid output increase and the change quantity before and after the rapid output decrease.

4. The filter malfunction determination apparatus according to claim 3, wherein the electronic control unit is further configured to:

determine whether the parameter value output from the sensor after the rapid output decrease is equal to or less than a predetermined output value, and clear the correction value to zero upon determination that the parameter value output from the sensor after the rapid output decrease is equal to or less than the predetermined output value.

5. The filter malfunction determination apparatus according to claim 4, wherein:

the sensor comprises a heater member configured to heat the particulate matter adhered to the sensor, and the electronic control unit is further configured to:

determine whether the parameter value output from the sensor is equal to or more than a predetermined acceptable value after the rapid output increase; and activate the heater member to heat the particulate matter upon determination that the parameter value output from the sensor is equal to or more than the acceptable value.

6. The filter malfunction determination apparatus according to claim 3, wherein:

the sensor comprises a heater member configured to heat the particulate matter adhered to the sensor, and the electronic control unit is configured to:

determine whether the parameter value output from the sensor is equal to or more than a predetermined acceptable value after the rapid output increase; and activate the heater member to heat the particulate matter upon determination that the parameter value output from the sensor is equal to or more than the acceptable value.

7. The filter malfunction determination apparatus according to claim 2, wherein the electronic control unit is further configured to:

determine whether the parameter value output from the sensor after the rapid output decrease is equal to or less than a predetermined output value, and clear the correction value to zero upon determination that the parameter value output from the sensor after the rapid output decrease is equal to or less than the predetermined output value.

8. The filter malfunction determination apparatus according to claim 7, wherein:

the sensor comprises a heater member configured to heat the particulate matter adhered to the sensor, and the electronic control unit is further configured to:

determine whether the parameter value output from the sensor is equal to or more than a predetermined acceptable value after the rapid output increase; and activate the heater member to heat the particulate matter upon determination that the parameter value output from the sensor is equal to or more than the acceptable value.

9. The filter malfunction determination apparatus according to claim 2, wherein:

the sensor comprises a heater member configured to heat the particulate matter adhered to the sensor, and the electronic control unit is further configured to:

determine whether the parameter value output from the sensor is equal to or more than a predetermined acceptable value after the rapid output increase; and activate the heater member to heat the particulate matter upon determination that the parameter value output from the sensor is equal to or more than the acceptable value.

10. The filter malfunction determination apparatus according to claim 1, wherein:

the sensor comprises a heater member configured to heat the particulate matter adhered to the sensor, and the electronic control unit is further configured to:

determine whether the parameter value output from the sensor is equal to or more than a predetermined acceptable value after the rapid output increase; and activate the heater member to heat the particulate matter upon determination that the parameter value output from the sensor is equal to or more than the acceptable value.

11. The filter malfunction determination apparatus according to claim 1, wherein:

the sensor comprises a heater member configured to heat the particulate matter adhered to the sensor;

the electronic control unit is further configured to:

repeatedly perform determination of whether the rapid output increase has occurred, the rapid output increase representing that the amount of increase of the parameter value per unit time output from the sensor has exceeded the predetermined value;

count the number of times it is determined that the rapid output increase has occurred; and cause the heater to heat the particulate matter upon the number of times counted by the counter unit reaching a predetermined number.

12. The filter malfunction determination apparatus according to claim 1, wherein: when the electronic control unit determines that there is the malfunction in the filter device upon the determination that the parameter value output from the sensor has reached the predetermined malfunction determination threshold, the electronic control unit uses, in the determination, the offset corrected parameter value output from the sensor as the parameter value output from the sensor and/or the offset corrected malfunction determination threshold as the malfunction determination threshold.

* * * * *